US010161790B2

United States Patent
Ding et al.

(10) Patent No.: US 10,161,790 B2
(45) Date of Patent: Dec. 25, 2018

(54) DELAY LINE DEVICE AND TERAHERTZ TIME-DOMAIN SPECTROMETER SYSTEM

(71) Applicants: Shenzhen Institute of Terahertz Technology and Innovation, Shenzhen, Guangdong (CN); Shenzhen Terahertz System Equipment Co., Ltd., Shenzhen, Guangdong (CN)

(72) Inventors: Qing Ding, Guangdong (CN); Shichang Peng, Guangdong (CN); Yi Pan, Guangdong (CN); Chen Li, Guangdong (CN)

(73) Assignees: Shenzhen Institute of Terahertz Technology and Innovation, Shenzhen, Guangdong (CN); Shenzhen Terahertz System Equipment Co., Ltd., Shenzhen, Guangdong (CN)

( * ) Notice: Subject to any disclaimer, the term of this patent is extended or adjusted under 35 U.S.C. 154(b) by 0 days.

(21) Appl. No.: 15/768,714

(22) PCT Filed: Aug. 10, 2017

(86) PCT No.: PCT/CN2017/096773
§ 371 (c)(1),
(2) Date: Apr. 16, 2018

(87) PCT Pub. No.: WO2018/054182
PCT Pub. Date: Mar. 29, 2018

(65) Prior Publication Data
US 2018/0274978 A1    Sep. 27, 2018

(30) Foreign Application Priority Data
Sep. 26, 2016    (CN) .......................... 2016 1 0852715

(51) Int. Cl.
*G01J 3/02*    (2006.01)
*G01J 3/06*    (2006.01)
(Continued)

(52) U.S. Cl.
CPC ............... *G01J 3/0208* (2013.01); *G01J 3/06* (2013.01); *G01J 3/42* (2013.01); *G01N 21/3586* (2013.01);
(Continued)

(58) Field of Classification Search
CPC ........ G01J 3/02; G01J 3/06; G01J 3/42; G01J 3/45; G01J 5/02; G01N 21/35
See application file for complete search history.

(56) References Cited

U.S. PATENT DOCUMENTS

| 8,546,762 B1 | 10/2013 | Roehle et al. |
| 2011/0235046 A1 | 9/2011 | Maruyama et al. |
| 2016/0116553 A1* | 4/2016 | Kim ..................... G01R 33/032 324/305 |

FOREIGN PATENT DOCUMENTS

| CN | 103575393 A | 2/2014 |
| CN | 204188262 U | 3/2015 |

(Continued)

*Primary Examiner* — Abdullahi Nur
(74) *Attorney, Agent, or Firm* — Young Basile Hanlon & MacFarlane, P.C.

(57) ABSTRACT

A delay line device and a terahertz time-domain spectrometer system include: a baseplate, a slide rail component, in which the slide rail component includes a slide, a reflector, a grating ruler component, and an electric-magnetic induction component. When the electric-magnetic component, after being applied a current, cuts the magnetic induction coil to generate power to push the slide moving, the grating ruler component placed on the slide rail component collects the movement information of the slide. The slide's movement drives the reflector placed on the slide to move together (Continued)

to change the optical distance of a pump light, so as to generate the delay between the pump light and a probe light.

9 Claims, 3 Drawing Sheets

(51) Int. Cl.
    *G01N 21/3586*     (2014.01)
    *G01J 3/42*     (2006.01)

(52) U.S. Cl.
    CPC ... *G01J 2003/064* (2013.01); *G01J 2003/423* (2013.01)

(56) References Cited

FOREIGN PATENT DOCUMENTS

| | | |
|---|---|---|
| CN | 106323465 A | 1/2017 |
| CN | 206223295 U | 6/2017 |

\* cited by examiner

DELAY LINE DEVICE AND TERAHERTZ TIME-DOMAIN SPECTROMETER SYSTEM

CROSS-REFERENCE TO RELATED APPLICATION(S)

This application is a 371 application of International Application No. PCT/CN2017/096773, filed on Aug. 10, 2017, which claims priority to Chinese Patent Application No. 201610852715.9, filed on Sep. 26, 2016, the content of which is hereby incorporated by reference in its entirety.

TECHNICAL FIELD

Aspects of the present disclosure relate to the terahertz technology field, and more particularly, to a delay line device and a terahertz time-domain spectrometer system.

BACKGROUND

Terahertz time-domain spectrum technology is a far infrared coherent spectral measurement technology developed by D. H. Auston etc. on basis of antenna radiation mechanism in 1980s'. This technology respectively records terahertz time-domain electric field waveforms when there is a sample or not by terahertz radiation pulse passing through the sample or being reflected by the surface of the sample. Signals' frequency-domain waveforms, when there is a sample or not, are obtained from these two waveforms by means of fast Fourier transform. The detected sample's refractive index, dielectric constant, and absorption coefficient can be obtained by executing related mathematical calculation processing on the frequency-domain data. Compared with traditional spectroscopy technologies, the terahertz time-domain spectroscopy technology not only has broader measurement bandwidth, higher spectral resolution, and better spectral signal-to-noise ratio, but also can record the amplitude information and the phase information of the detected sample signal at the same time.

A typical terahertz time-domain spectrometer system comprises a femtosecond pulse laser, a terahertz radiation device, a terahertz detection device, and a delay line device. A traditional delay line device is generally based on a stepping motor to build a set of symmetrical reflectors to achieve optical path's 180-degree reversal, and then the delay adjustment of a pump light path and a probe light path is implemented by a motor controller. However, this device has the inherent defects of heavy, large area occupation, and no modular integration, so that it is not suitable for the terahertz time-domain spectrometer system with the characteristics of commercialization, miniaturization, and portable.

SUMMARY

In view of the above, with respect to this problem, it is necessary to provide a delay line device and a terahertz time-domain spectrometer system with modular miniaturization and convenient to be manufactured and integrated.

A delay line device for adjusting the time signal delay between a pump light and a probe light, comprising: a baseplate bearing weight; a slide rail component mounted on the baseplate, wherein the slide rail component comprises a slide, which is movable relative to the baseplate; a reflector fixed on one end of the slide for realizing the pump light's 180-degree reversal; a grating ruler component placed on the slide rail component for collecting the movement information of the slide; an electric-magnetic induction component comprising an induction coil, wherein the induction coil is connected to the second end of the slide, and the electric-magnetic induction component is used to provide power to drive the slide to move.

According to one embodiment, the slide rail component also comprises a slide rail base, which is fixed on the baseplate; and a groove is provided on the slide rail base, and the slide is placed in the groove.

According to one embodiment, the reflector is a backward reflector.

According to one embodiment, the grating ruler component comprises: a scale grating, which is fixed on the top surface of the slide for measuring the movement information of the slide; a grating reading head, which is correspondingly placed over the scale grating, and is parallel and equidistant to the scale grating for coordinating with the scale grating to collect the movement information of the slide; a fixed block, wherein two ends of the fixed block are respectively connected to the baseplate and the grating reading head for fixing the grating reading head to the baseplate.

According to one embodiment, the distance between the grating reading head and the scale grating is 2.4 mm to 2.6 mm.

According to one embodiment, the electric-magnetic induction component comprises: an induction coil, which is used to cut the magnetic induction lines after being applied a current, to generate power to drive the slide to move; a magnet, wherein the induction coil is nested in the magnet, and the magnet is used to generate a stable magnetic field; a magnet supporting seat, which is connected to the magnet to support it, so that the magnet and the induction coil are coaxially placed.

According to one embodiment, the delay line device also comprises a substrate and an adjusting plate, both the baseplate and the magnet supporting seat are placed on the substrate, the adjusting plate is placed on the substrate opposite to the baseplate, and the adjusting plate is used to adjust the height of the delay line device.

According to one embodiment, a plurality of sliding channels are provided on the baseplate for receiving a fastening piece, so that the baseplate is movable relative to the substrate.

According to one embodiment, the delay line device also comprises a fixed part, wherein the fixed part is connected to the adjusting plate for fixing the delay line device to a work platform.

In addition, this disclosure also provides a terahertz time-domain spectrometer system, comprising: a femtosecond pulse laser, which is used to radiate a femtosecond laser; a beam splitter, which is used to split the femtosecond laser into a pump light and a probe light; a terahertz radiation device, which is placed in the light path of the pump light to generate a terahertz radiation; a terahertz probe device, which is used to probe the terahertz pulse signal output by the terahertz radiation device, the terahertz time-domain spectrometer system also comprises the delay line device mentioned above for adjusting the time signal delay between the pump light and the probe light.

The above delay line device comprises a baseplate, a slide rail component, wherein the slide rail component comprises a slide, a reflector, a grating ruler component, and an electric-magnetic induction component. The pump light path's 180-degree reversal is achieved by radiating on the reflector. When the electric-magnetic component, after being applied a current, cuts the magnetic induction coil to generate power to push the slide moving, the grating ruler component placed on the slide rail component collects the movement information of the slide. The slide's movement will drive the reflector placed on the slide to move to change the optical distance of the pump light, so as to generate the delay between the pump light and the probe light. Applying the electric-magnetic induction component in the delay line device to drive the slide to move can realize fast scan. Furthermore, compared collecting the movement information of the slide by the grating ruler component with measuring movement by a stepping motor, the grating ruler component has the advantages of higher precision, better stability, faster response, and stronger anti-interference ability. Meanwhile, since the delay line device is assembled by the way of modular integration, it has a compact structure and saves space, which is beneficial for structure miniaturization.

DETAILED DESCRIPTION

In order to make the objectives, technical solutions and advantages of the disclosure to be clearer, the disclosure is further described in conjunction with appended drawings and embodiments. It should be understood that the specific embodiments described herein are used only to explain the present disclosure and are not intended to limit the disclosure.

Unless otherwise defined, all technology and science terminologies herein have the same meanings commonly understood by persons skilled in this field to which this disclosure belongs. Terminologies used in this specification of the disclosure are merely intended to describe specific embodiments and are not limited to this disclosure. The phrase "and/or" used herein comprises arbitrary and all the combinations of one or more related listed items.

Figure 1:
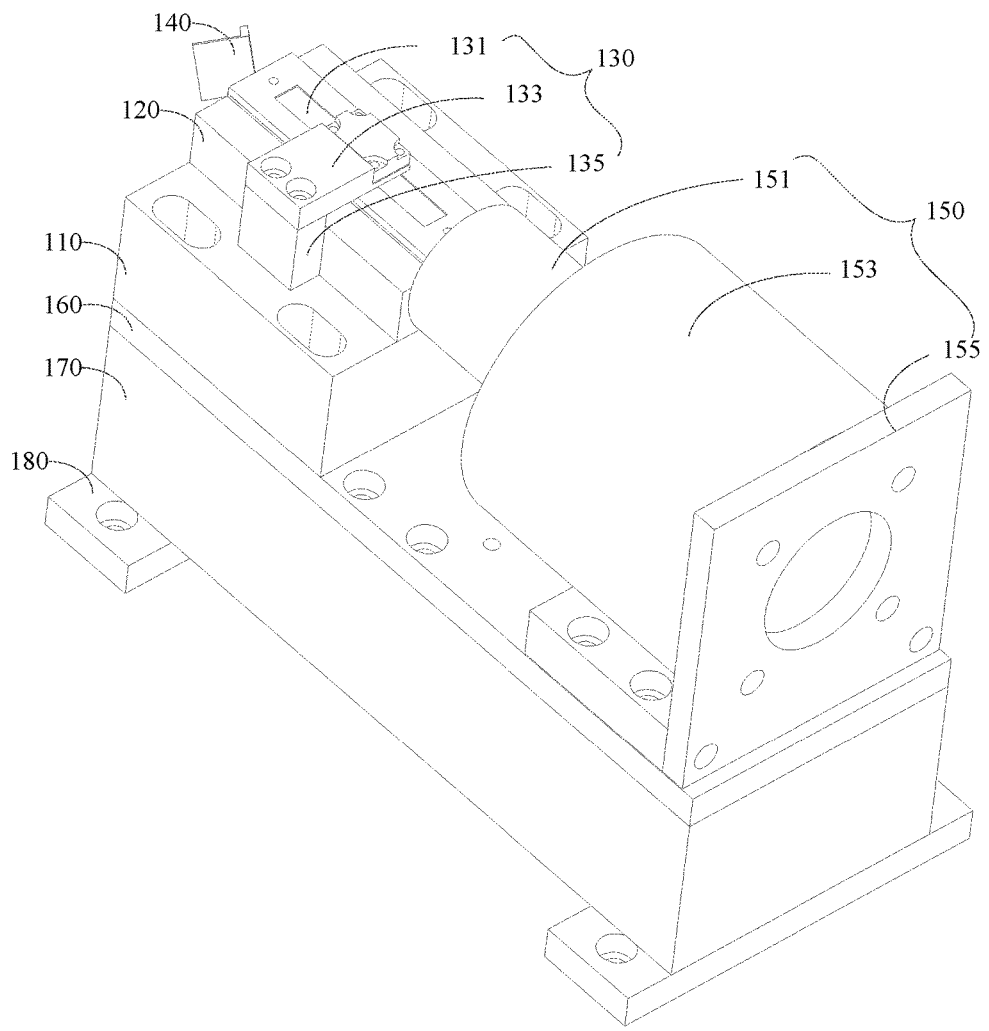
FIG. 1 illustrates a structural diagram of a delay line device in an embodiment.

FIG. 1 illustrates a structural diagram of a delay line device in an embodiment. A delay line device 10 is placed in the optical path of a pump light for adjusting the time signal delay of the pump light and the probe light. The delay line device 10 comprises a baseplate 110, a slide rail component 120, wherein the slide rail component 120 comprises a slide 121, a grating ruler component 130, a reflector 140, and an electric-magnetic induction component 150. A pump light radiates on the reflector 140 to achieve 180-degree reversal. After being applied a current, the electric-magnetic induction component 150 cuts the magnetic induction coil to generate power to push the slide 121 to move. The grating ruler component 130 placed on the slide rail component 120 collects the movement information of the slide 121. The movement of the slide 121 will drive the reflector 140 placed on the slide 121 to move together to change the optical distance of the pump light, so as to generate the delay between the pump light and the probe light. When the slide 121 moves one micron, the delay between the pump light and the probe light is 6.67 femtosecond, i.e., $\Delta\tau=[(1+1)*10^{-6}\,(m/s)]/[3*10^{8}\,(m/s)]=6.67*10^{-15}\,(s)$.

By the power provided by the electric-magnetic induction component 150 to drive the slide 121, the delay line device 10 can realize fast scan. Furthermore, comparing collecting the movement information of the slide 121 by the grating ruler component 130 with measuring movement by a stepping motor, the grating ruler component 130 has the advantages of higher precision, better stability, faster response, and stronger anti-interference ability. Furthermore, since the delay line device 10 is assembled by the way of module integration, it has compact structure and saves space, which is beneficial for structure miniaturization.

The baseplate 110 is used to bear the slide rail component 120. The slide rail component 120 is connected to the baseplate 110 by an installing pole in the baseplate 110. If the reflector 140 or the grating ruler component 130 on the slide rail component 120 occurs an exception or breaks down, the baseplate 110 needs to be disassembled, which is convenient to maintain.

Figure 2:
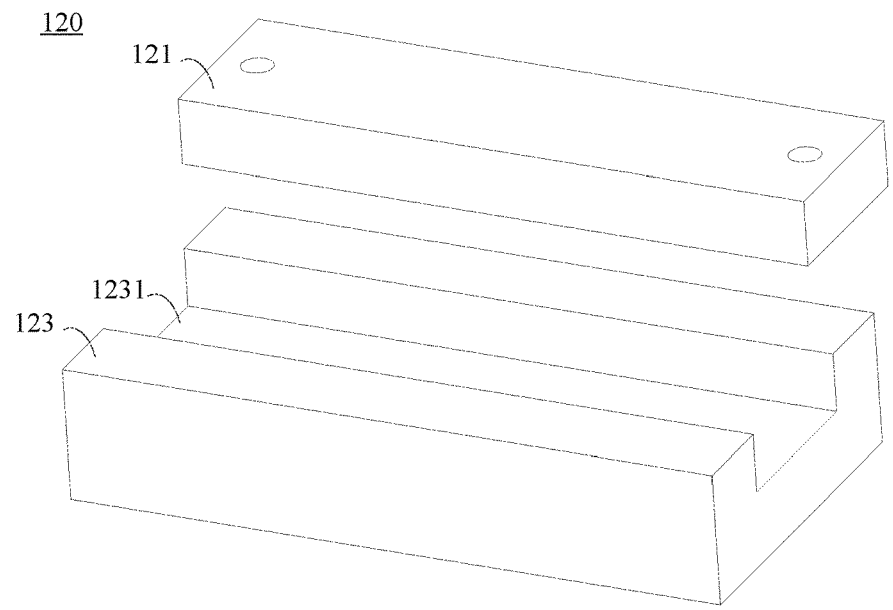
FIG. 2 illustrates a structural diagram of a slide rail component in an embodiment.

FIG. 2 illustrates a structural diagram of the slide rail component 120. The slide rail component 120 also comprises a slide rail base 123, which is fixed on the baseplate 110. A groove 1231 is provided on the slide rail base 123, and the slide 121 is placed in the groove 1231. When the electric-magnetic induction component 150 pushes the slide 121, the slide 121 moves along the groove 1231.

The grating ruler component 130 is placed on the slide rail component 120 for collecting the movement information of the slide 121. The grating ruler component 130 comprises a scale grating, a grating reading head, and a fixed block.

The scale grating is fixed on the top surface of the slide 121 for measuring the movement information of the slide 121. In this embodiment, the scale grating is embedded in the slide 121, so that the top surface of the scale grating has the same level as that of the slide 121. In this embodiment, the scale grating is a steel belt scale with high precision. The grating reading head is correspondingly placed over the middle position of the scale grating, and is parallel and equidistant to the scale grating for coordinating with the scale grating to collect the movement information of the slide 121.

The distance between the grating reading head and the scale grating is 2.4 mm to 2.6 mm. In this embodiment, the distance between the grating reading head and the scale grating is 2.5 mm. In this distance, collecting the scale grating data by the grating reading head has the strongest signal, good stability, fast response, and strong anti-interference ability.

Two ends of the fixed block are respectively connected to the baseplate 110 and the grating reading head for fixing the grating reading head to the baseplate 110. In this embodiment, the fixed block is a light aluminum block, which can reduce the whole weight of the delay line device 10. The fixed block is perpendicularly fixed on the baseplate 110, and the fixed block is connected to the grating reading head through a fastening piece, in "L" form, so as to ensure that the grating reading head is parallel to the scale grating and the grating reading head is static relative to the baseplate 110. When the slide 121 moves, it drives the scale grating placed therein to move. The grating reading head is static relative to the baseplate 110 through the fixed block. That is, when the slide 121 moves, the scale grating moves relative to the baseplate 110, and the grating reading head is static relative to the baseplate 110. That is, when the slide 121 moves, the scale grating also moves relative to the baseplate 110, and the grating reading head is static relative to the baseplate 110. That is, the grating ruler component 130 can collect the movement information of the slide 121.

In an embodiment, the reflector 140 is a backward reflector. The backward reflector is formed by perpendicularly bonding the three reflectors in pairs. The backward reflector is set to realize the 180° reversal of the pump light. In other embodiments, the reflector 140 may be a set of symmetric reflectors 140. Setting two symmetric reflectors can also realize the 180° reversal of the pump light.

The electric-magnetic induction component 150 comprises an induction coil 151. The induction coil 151 is connected to the second end of the slide 121. The electric-magnetic induction component 150 is used to provide power to drive the slide 121 to move. The electric-magnetic induction component 150 comprises an induction coil 151, a magnet 153, and a magnet supporting seat 155. After being applied a current, the induction coil 151 is used to cut the magnetic induction lines to generate magnetic field. The induction coil 151 is nested in the magnet 153. The stable magnetic field generated by the magnet 153 interacts with the magnetic field generated by the induction coil 151 after being applied a current to push the slide 121. The magnet supporting seat 155 is connected to the magnet 153 to support it, so that the magnet 153 and the induction coil 151 are coaxially placed. That is, the center height of the magnet 153 is the same as that of the induction coil 151. After being applied a current, the driving force generated by the electric-magnetic induction component 150 is in horizontal direction. The magnet supporting seat 155 is also light aluminum.

The delay line device 10 also comprises a substrate 160 and an adjusting plate 170. Both the baseplate 110 and the magnet supporting seat 155 are placed on the substrate 160. The baseplate 110 and the magnet supporting seat 155 are fixed on the substrate 160, so that they are integrated. When the operating environment is changed, there is no need to calibrate the delay line device 10, which is convenient to operate.

The delay line device 10 also comprises an adjusting plate 170. The adjusting plate 170 is placed on the substrate 160, opposite to the baseplate 110. The adjusting plate 170 is used to adjust the height of the delay line device. When the system comprising the pump light to be delayed and the probe light changes, it need not to adjust other components of the delay line device 10 but only to change the thickness of the adjusting plate 170 to adapt this change, which is adaptable and can be widely applied in different delay systems.

Figure 3:
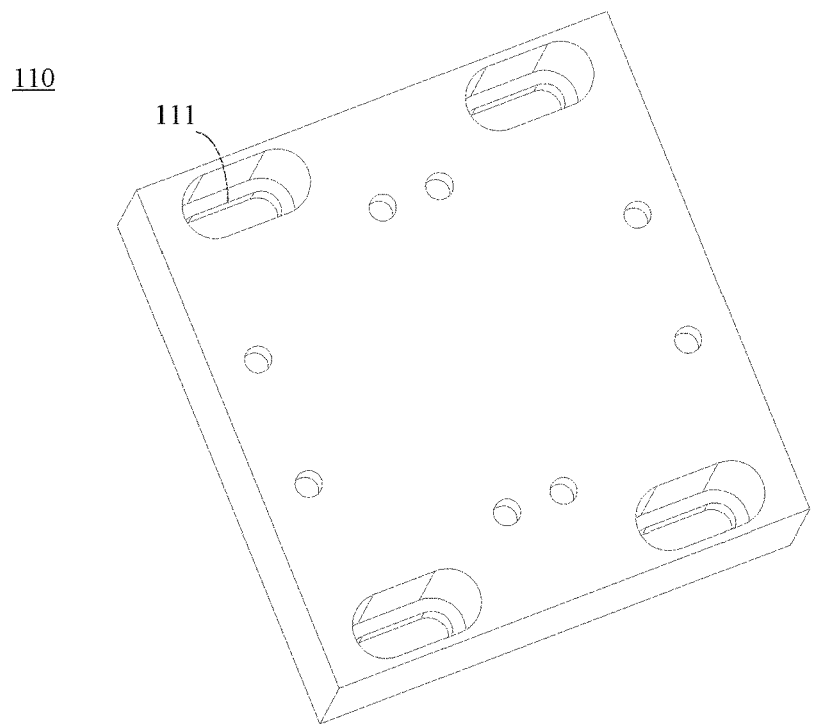
FIG. 3 illustrates a structural diagram of a baseplate in an embodiment.

In an embodiment, referring to FIG. 3, a plurality of sliding channels 111 are provided on the baseplate 110 for receiving the fastening piece, so that the baseplate 110 can move relative to the substrate 160. The number of the sliding channels 111 is four, and the sliding channels are respectively provided at the four corners of the baseplate 110. The number and the location of the sliding channels 111 are not limited to this, which can be set according to actual needs. When the fastening piece in the sliding channels 111 is locked, the baseplate 110 and the substrate 160 are permanently connected. If in a special scenario that the movement displacement of the slide 121 is greater than a preset amount of this device, the fastening piece in the sliding channels 111 is loosened slightly, so that the baseplate 110 can move relative to the substrate 160 to extend the displacement of the slide 121. Components on the slide rail component 120 need not to be repositioned, so that it has wide application scenarios and high efficiency.

The delay line device 10 also comprises a fixed part 180. The fixed part 180 is connected to the adjusting plate 170 for fixing the delay line device 10 to a work platform. In this embodiment, the fixed part 180 comprises a plurality of fixed feet placed at the two ends of the adjusting plate 170. In other embodiments, in order to ensure the horizontal and stability of the delay line device 10, the fixed part 180 can also be a plurality of screw feet. In order to adapt to different work platform, heights of different screw feet can be adjusted to keep the delay line device 10 horizontal and stability.

Figure 4:
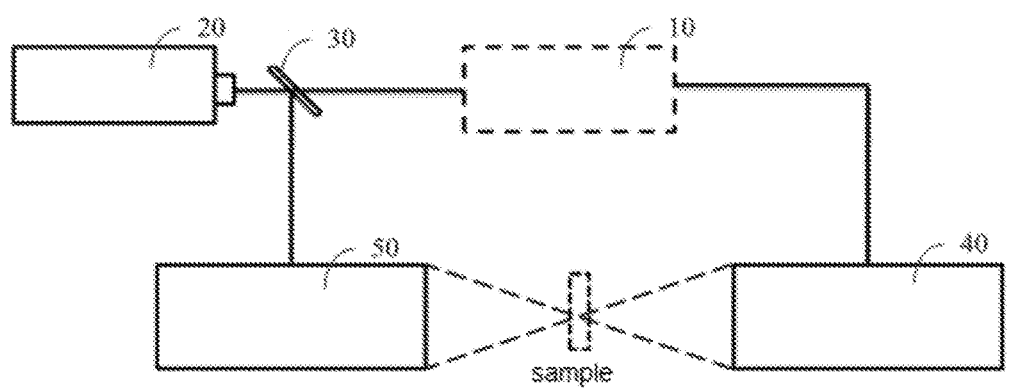
FIG. 4 illustrates a terahertz time-domain spectrometer system in an embodiment.

In addition, this disclosure also provides a terahertz time-domain spectrometer system. Referring to FIG. 4, the terahertz time-domain spectrometer system comprises a femtosecond pulse laser, a beam splitter, the delay line device 10, a terahertz radiation device, and a terahertz probe device. The femtosecond pulse laser is used to radiate a femtosecond laser. The beam splitter is used to split the femtosecond laser into a pump light and a probe light. The delay line device 10 is placed in the light path of the pump light to adjust the time signal delay of the pump light and the probe light. The terahertz radiation device is placed in the light path of the pump light to generate a terahertz radiation. The terahertz probe device is used to probe the terahertz pulse signal output by the terahertz radiation device.

Specifically, the femtosecond laser pulse radiated by the femtosecond laser is split into two beams by the beam splitter, wherein one is a pump light and the other is a probe light. After the pump light passing through the delay line device 10, an adjustable time delay (respective to the probe light) is generated, and then the pump light enters the terahertz radiation device to generate a terahertz pulse with the time scale of picosecond ($10^{-12}$ s). After passing through a sample, the terahertz pulse and the probe light with time scale of femtosecond ($10^{-15}$ s) enter the terahertz probe device synchronously. Since the time scale of the probe light is very small with respect to the terahertz pulse, it can be deemed as a point pulse, and the delay line device 10 moving 1 micron corresponds to a delay of 6.67 femtoseconds ($6.67*10^{-15}$). While the delay line device 10 scans some distance, the terahertz probe device can take samples of the terahertz signal point by point, so as to record the whole terahertz waveform. Furthermore, setting the above delay line device 10 can provide a terahertz time-domain spectrometer system with high precision.

The technical features in the above embodiments can be combined arbitrarily. For simplicity, not all possible combinations of the technical features in the above embodiments are described. However, these combinations of the technical features should be within the scope recited in this specification, provided that there is no conflict in these combinations of the technical features.

The above embodiments merely express several implementing ways specifically and in detail. However, this cannot be constructed as a limit to the scope of this disclosure. It should be noted that, persons skilled in the art can make many variations and modifications without departing from the spirit of this disclosure, all of which belong to the scope of this disclosure. Therefore, the scope of the present application should be determined by the terms of the accompanying claims.

What is claimed is:
1. A delay line device for adjusting the time signal delay between a pump light and a probe light, comprising:
   a baseplate bearing weight;

a slide rail component mounted on the baseplate, wherein the slide rail component comprises a slide, which is movable relative to the baseplate;
a reflector fixed on one end of the slide for realizing the pump light's 180-degree reversal, wherein the reflector is a backward reflector;
a grating ruler component placed on the slide rail component for collecting the movement information of the slide; and
an electric-magnetic induction component comprising an induction coil, wherein the induction coil is connected to the second end of the slide, and the electric-magnetic induction component is used to provide power to drive the slide to move.

2. The delay line device of claim 1, wherein the slide rail component also comprises a slide rail base, which is fixed on the baseplate; and wherein a groove is provided on the slide rail base, and the slide is placed in the groove.

3. The delay line device of claim 1, wherein the grating ruler component comprises:
a scale grating, which is fixed on the top surface of the slide for measuring the movement information of the slide;
a grating reading head, which is correspondingly placed over the scale grating, and is parallel and equidistant to the scale grating for coordinating with the scale grating to collect the movement information of the slide; and
a fixed block, wherein two ends of the fixed block are respectively connected to the baseplate and the grating reading head for fixing the grating reading head to the baseplate.

4. The delay line device of claim 3, wherein the distance between the grating reading head and the scale grating is 2.4 mm to 2.6 mm.

5. The delay line device of claim 1, wherein the electric-magnetic induction component comprises:
an induction coil, which is used to cut the magnetic induction lines after being applied a current, to generate power to drive the slide to move;
a magnet, wherein the induction coil is nested in the magnet, and the magnet is used to generate a stable magnetic field; and
a magnet supporting seat, which is connected to the magnet to support it, wherein the magnet and the induction coil are coaxially placed.

6. The delay line device of claim 5, wherein the delay line device also comprises a substrate and an adjusting plate, the baseplate and the magnet supporting seat are placed on the substrate, the adjusting plate is placed on the substrate opposite to the baseplate, and the adjusting plate is used to adjust the height of the delay line device.

7. The delay line device of claim 6, wherein a plurality of sliding channels is provided on the baseplate for receiving a fastening piece, wherein the baseplate is movable relative to the substrate.

8. The delay line device of claim 6, wherein the delay line device further comprises a fixed part, wherein the fixed part is connected to the adjusting plate for fixing the delay line device to a work platform.

9. A terahertz time-domain spectrometer system, comprising:
a femtosecond pulse laser, which is used to radiate a femtosecond laser;
a beam splitter, which is used to split the femtosecond laser into a pump light and a probe light;
a terahertz radiation device, which is placed in the light path of the pump light to generate a terahertz radiation; and
a terahertz probe device, which is used to probe the terahertz pulse signal output by the terahertz radiation device, the terahertz time-domain spectrometer system further comprises the delay line device according to claim 1 for adjusting the time signal delay between the pump light and the probe light.

* * * * *